(12) United States Patent
Laghi et al.

(10) Patent No.: US 8,979,944 B2
(45) Date of Patent: *Mar. 17, 2015

(54) METHOD APPARATUS OF A LINER INTERFACE WITH NEURAL RECEPTORS

(71) Applicant: ALPS South, LLC, St. Petersburg, FL (US)

(72) Inventors: Aldo A. Laghi, Pinellas Park, FL (US); Kevin McLoone, Dunedin, FL (US)

(73) Assignee: ALPS South, LLC, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/687,229

(22) Filed: Nov. 28, 2012

(65) Prior Publication Data

US 2014/0148916 A1    May 29, 2014

(51) Int. Cl.
*A61F 2/48* (2006.01)
*A61F 2/78* (2006.01)
(Continued)

(52) U.S. Cl.
CPC .............. *A61F 2/7812* (2013.01); *H01R 43/00* (2013.01); *A61B 5/04* (2013.01)
USPC .................... 623/25; 623/24; 623/32; 623/36

(58) Field of Classification Search
CPC ............. A61B 5/04001; A61B 5/6811; A61B 5/6824; A61B 5/6828; A61F 2002/5064; A61F 2/70; A61F 2/72; A61F 2/7812
USPC ................ 623/24, 25, 36; 600/384, 386, 393; 607/149, 152
See application file for complete search history.

(56) References Cited

U.S. PATENT DOCUMENTS 5,213,715 A    5/1993  Patterson et al.
5,258,037 A *  11/1993 Caspers .......................... 623/36
(Continued)

FOREIGN PATENT DOCUMENTS

DE    102007035409 A1    1/2009
EP         2737878 A1    4/2014

OTHER PUBLICATIONS

Daly. Clinical Application of Roll-on Sleeves for Myoelectrically Controlled Transradial and Transhumeral Prostheses. Journal of Prosthetics and Orthotics. vol. 12, No. 3. pp. 88-91.*

(Continued)

*Primary Examiner* — Thomas J Sweet
*Assistant Examiner* — Christie Bahena
(74) *Attorney, Agent, or Firm* — Shumaker, Loop & Kendrick, LLP; Jason A. Smith

(57) ABSTRACT

A liner interface and method of making comprising non-compressible deformable electrically conductive neural receptors having electrically conductive elements extending therefrom, formed by attaching each receptor and the conductive elements to an inner surface of a fabric layer, placing the fabric layer into a first part of a molding machine having a predetermined shape, moving a second part of the molding machine having a shape complemental to the first predetermined shape toward said fabric layer to either abut or axially deform the deformable receptors and define a space therebetween, injecting a molten gel elastomer into the space to surround and adhere to the receptors, conductive elements and fabric layer, allowing the molten gel to cure to form a gel inner surface, and removing the second part from the molding machine and allowing the receptors to either axially expand beyond or remain even with the inner surface of the cured liner interface.

68 Claims, 4 Drawing Sheets

(51) Int. Cl.
*A61F 2/80* (2006.01)
*A61F 2/70* (2006.01)
*H01R 43/00* (2006.01)
*A61B 5/04* (2006.01)

(56) References Cited

U.S. PATENT DOCUMENTS

| | | | |
|---|---|---|---|
| 5,376,132 | A | 12/1994 | Caspers |
| 5,443,525 | A | 8/1995 | Laghi |
| 5,507,834 | A * | 4/1996 | Laghi ............... 623/36 |
| 5,785,040 | A * | 7/1998 | Axelgaard ............ 600/391 |
| 6,852,269 | B2 | 2/2005 | Eberle et al. |
| 8,024,023 | B2 | 9/2011 | Tolvanen |
| 8,591,599 | B1 * | 11/2013 | Kaliki et al. ............ 623/25 |
| 2005/0101693 | A1 * | 5/2005 | Arbogast et al. .......... 523/122 |
| 2009/0132056 | A1 | 5/2009 | Kania |
| 2009/0216339 | A1 * | 8/2009 | Hanson et al. .......... 623/25 |
| 2010/0004524 | A1 | 1/2010 | Yuen |
| 2010/0114238 | A1 | 5/2010 | Muccio |
| 2010/0318195 | A1 | 12/2010 | Kettwig et al. |
| 2011/0270414 | A1 * | 11/2011 | Laghi et al. ............ 623/36 |
| 2012/0190989 | A1 | 7/2012 | Kaiser et al. |
| 2012/0253475 | A1 | 10/2012 | Kelley |
| 2012/0296445 | A1 * | 11/2012 | Leiniger et al. .......... 623/25 |
| 2013/0046392 | A1 * | 2/2013 | Venu et al. ............ 623/23.53 |
| 2013/0331950 | A1 * | 12/2013 | Laghi et al. ............ 623/36 |

OTHER PUBLICATIONS

ABB. Silicone Rubber Product Information. May 15, 2005.*
Dupont Tyvek Products. Verified by the Wayback Machine Aug. 6, 2012.*
Ossur (pp. 1 and 2) (Iceross Original Locking Liner) Verified by the Wayback Machine Dec. 21, 2010.*
European Search Report Application No. 13 19 4821 (attached).

* cited by examiner

Prior Art

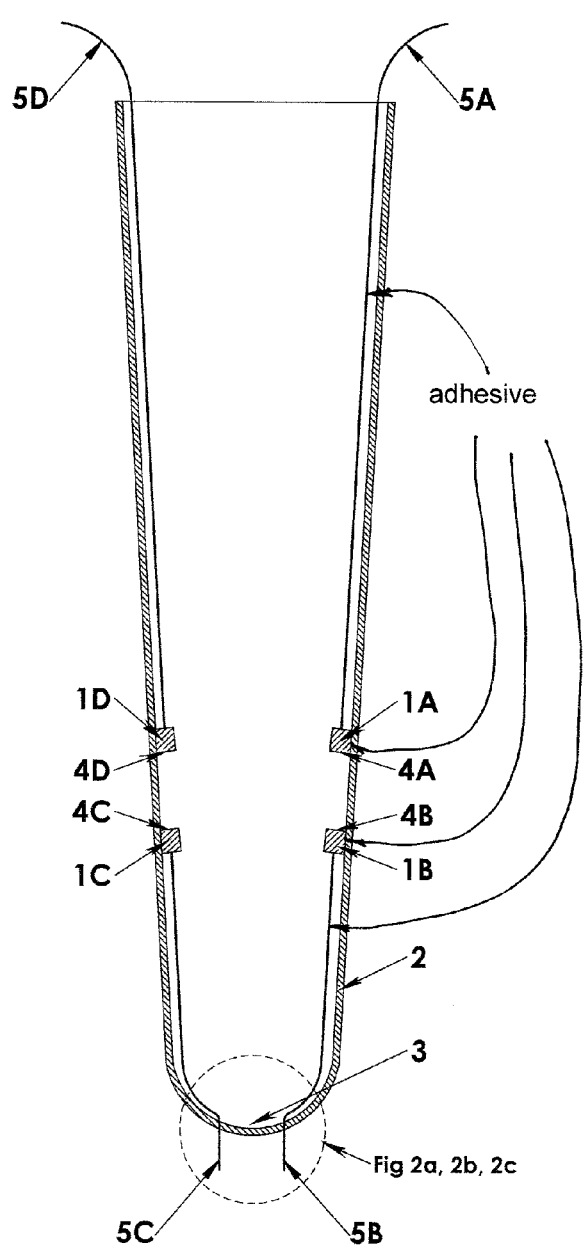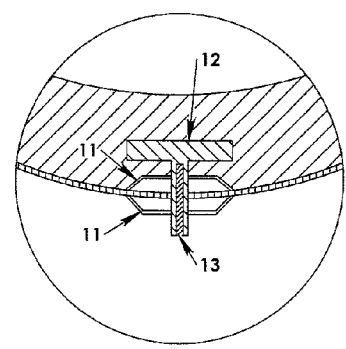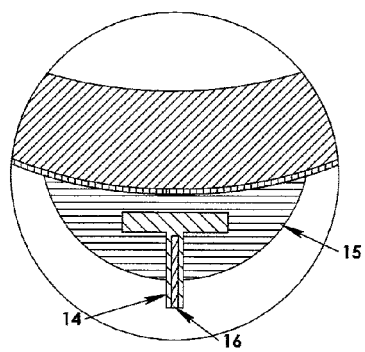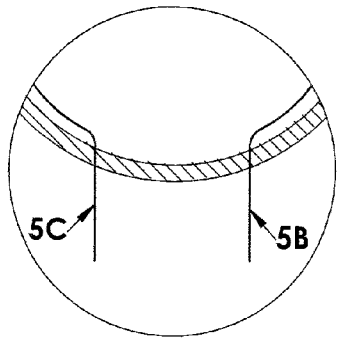

METHOD APPARATUS OF A LINER INTERFACE WITH NEURAL RECEPTORS

CROSS-REFERENCE TO RELATED APPLICATIONS

Not applicable.

STATEMENT REGARDING FEDERALLY SPONSORED RESEARCH OF DEVELOPMENT

Not applicable.

PARTIES TO A JOINT RESEARCH AGREEMENT

This application is a result of activities undertaken within the scope of a joint research agreement between Alps South, LLC and the Rehabilitation Institute of Chicago that was in effect on or before the date of the research leading to this application was made.

INCORPORATION-BY-REFERENCE OF MATERIAL SUBMITTED ON A COMPACT DISC

Not applicable.

BACKGROUND OF THE INVENTION

The present invention relates generally to a gel cushioned interface and a method of making a gel cushioned interface made of polymer material with heat resistant and electrically conductive neural receptors housed strategically within and potentially raised slightly above the inner surface of the polymer material to be worn over a limb or body surface for the purpose of conducting and/or receiving impulses through the interface.

The use of myoelectrics in the orthotics and prosthetics field started with the basic use of a conductive metal dome placed on a user's particular muscle group to pick up neural signals from nerve endings through the skin. With such a system, when the user would fire the bicep muscle, for example, the dome would pick up the signal and send it to the powered prosthesis telling it to create flexion in the prosthetic elbow. Many metal domes would be affixed to the skin of the end user externally and hard-wired (sometimes long distances) into the powered prosthetic device so that the user could fire off certain muscle groups to control functionality of the prosthesis.

More recent improvements to myoelectrics in the field involve using a series of metal domes that are punctured through and embedded in an otherwise traditional liner interface after the molding process, that are then connected to a CPU using external wires that control the powered prosthesis. Concurrently, other developments are taking place where metal electrodes are actually implanted into the user's pectoral muscle and hardwired to a CPU for cognitive control over the prosthesis.

The process of surgically inserting metal domes into a user is obviously a very invasive procedure that many potential users are unwilling to undergo. The post-molding process of puncturing holes into a liner to insert metal domes is also a difficult process that is time consuming and jeopardizes the original liner's structural integrity and durability. Thus, the need in the market exists for an interface liner that contains electrically conductive receptors that can make the appropriate amount of skin contact necessary to reliably pick up electrical impulses from very specific points on the user while also containing a means of transferring these impulses to a central processing unit.

One attempt that has been made to satisfy this need is disclosed in USPGPUB 20090216339 A1 to Hanson, et al., incorporated herein by reference. As best illustrated in FIG. 1 (10) or FIG. 2 (20), Hanson suggests affixing "domes" made of conductive silicone onto existing prosthetic liners after the molding process has taken place. Hanson focuses on the silicone dome's ability to create total contact on the skin surface, while also being properly affixed to the liner with an appropriate adhesive such as RTV silicone for silicone liners or moisture-activated urethane for urethane liners to form a more secure "butt joint" to hold the domes securely in place once they are added to the liner. USPGPUB 20100114238 A1 to Muccio incorporated herein by reference discloses a prosthetic liner, as best illustrated in FIGS. 1 and 2, having stimulation electrodes made of conductive hydrogel 105 integrated into the liner material during the molding process that are designed to be flush with the skin 106 on the inside of the liner and connected to a CPU by silver fabric conductors 103. USPGPUB 2010/0318195 A1 to Kettwig, et al. incorporated herein by reference discloses an orthopedic interface having electrically conductive coatings 23 on the inner fabric surface of the liner.

While these ideas seek to address the need for improving end user comfort while not jeopardizing functionality, they fail to address the need for a single off the shelf product that combines the manufacturability of having the electrodes molded into the inner material during a "one shot" manufacturing process while still allowing those same domes to provide an adequate amount of compression on the localized skin necessary to get a consistent myoelectric signal.

BRIEF SUMMARY OF THE INVENTION

The invention is made up of a gel cushioned liner with soft (10-40 durometer on type "A" scale) heat resistant silicone patches made of electrically conductive non-compressible deformable silicone material or electrically non-conductive non-compressible deformable elastomeric material covered in any number of conductive metals or materials (copper, silver, carbon, conductive fabric, etc.) molded into the interface liner during the manufacturing molding process. The terminology "axial deformation" or "axially deformable" herein is used to describe the reduction or expansion in thickness of the silicone patches. Silicone or elastomers, unlike foams or air, are incompressible and deformable in that they do not undergo a change in volume as they are deformed. The manufacturing process for a preferred embodiment of the invention is carried out by a conventional molding machine as, for example, illustrated in FIG. 1. During a molding process by the molding machine (10), the male core part (6) will be spaced from the female part (8) by a predetermined distance defining a predetermined annular space. A gel liner that serves as an ideal liner interface for housing the electrically conducive silicone components, while at the same time being as comfortable and minimally invasive as possible to the end user is the ALPS Gel Liner. During use of the liner, these patches are pressed against the skin of the end user to a degree that allows them to more reliably pick up neural impulses fired by nerve endings of particular muscles to aid in controlling a powered prosthesis.

The patches have an initial predetermined thickness greater than the annular space between the male and female parts of the molding machine. The patches are attached, for example by adhesive, at selected points on an interior surface of a tubular fabric layer designed as an outer fabric layer of a finished liner interface. As illustrated in FIGS. 2-4, a preferred embodiment of the present invention, although not limited thereto, includes a tubular fabric layer (2) illustrated to have a closed distal end and an open proximal end for a BK or AK liner. However, as stated above, the drawings are exemplary of a preferred use for the invention. Other uses could include arm prosthetics or other liners used on other body locations where it is desirable to monitor neural impulses for powering prosthetic and/or orthotic devices or simply monitoring for diagnostic purposes. After attaching the patches, the fabric layer (2) is placed in the female part of the molding machine. The male core part is then mated with the female part wherein the patches are axially deformed a slight distance and the annular space is closed. Next, a molten gel material (silicone, other TPE elastomers, copolymer Styrenic gels, polyurethane gel, etc.) is injected into the annular space to completely fill the annular space thereby adhering to the tubular fabric layer and around the patches, while leaving their surface area against the male part free of any molten material. When the liner is cured and removed from the molding machine, the patches are free to axially deform by expanding slightly from 0.0" to 0.25" beyond the inner surface of the cured gel layer and thereby toward the skin of the end user when in use so that the patches can have direct contact with the subcutaneous tissue superficial to the nerve that is strong enough to ensure a solid and consistent signal at all times, while still being soft enough to promote end user comfort.

The neural impulses can then be linked back through the conductive patches and into a CPU of the prosthetic via a network made up of any number of flexible materials exhibiting very low levels of resistivity (carbon filament, copper filament, silver thread, carbon fabric, copper fabric, silver fabric, traditional light gauge wire, etc.) that are also integrated into the inner gel portion of the liner interface as discussed hereinafter.

BRIEF DESCRIPTIONS OF THE SEVERAL VIEWS OF THE DRAWING(S)

FIG. 2 is a sectional view of the liner interface of a preferred embodiment of the present invention with the silicone patches adhered to the inside surface of the outer tubular fabric layer of the liner interface before the injection molding process.

FIG. 2a and FIG. 2b are enlarged sectional views of alternative distal encapsulations (3) circled in FIG. 2 that could be attached to the distal end of a preferred embodiment of the present invention.

FIG. 2c is an enlarged sectional view of an alternative distal end of the cushioned interface of FIG. 2 that could be used as an alternative to the distal encapsulations in FIGS. 2a and 2b.

Figure 1:
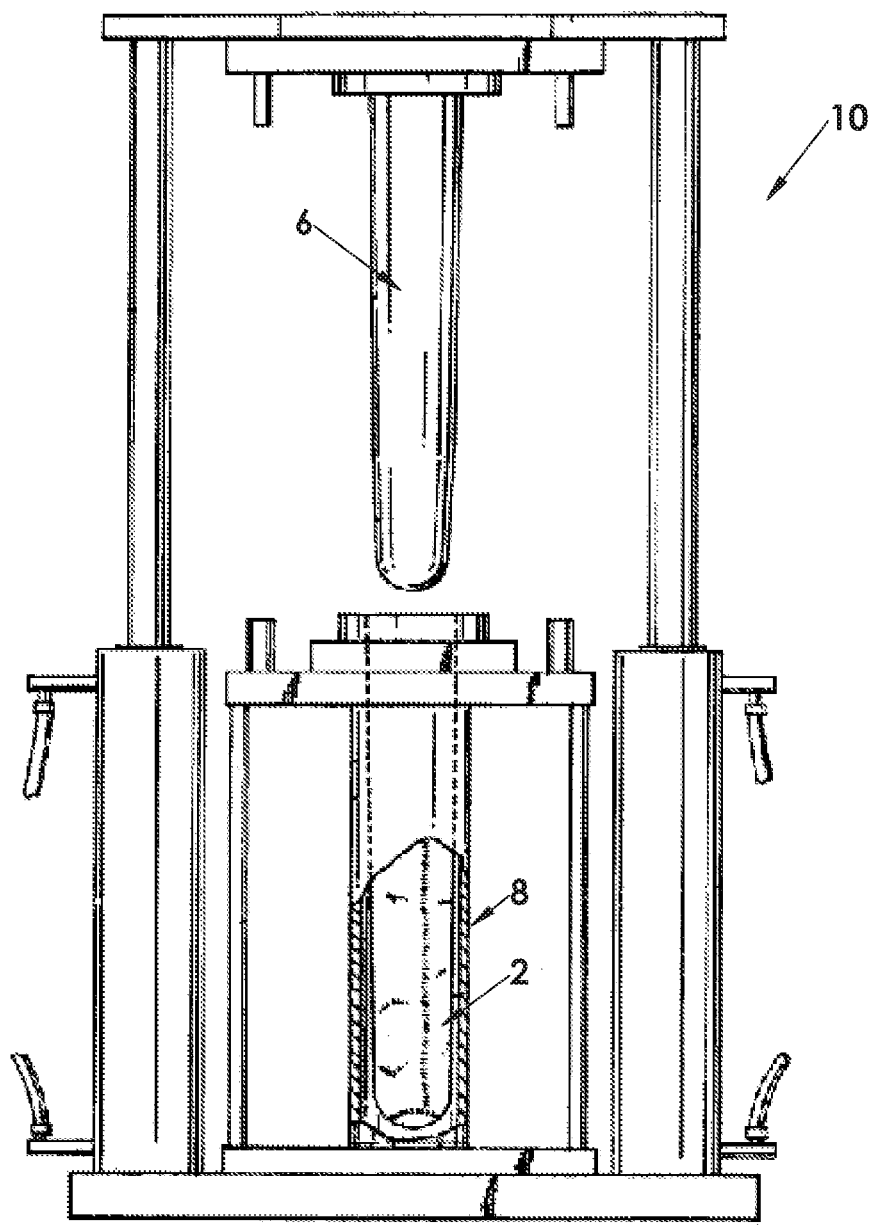
FIG. 1 shows a conventional molding machine of the same design that can be used to manufacture a prosthetic liner interface, which is a preferred embodiment of the present invention.
Figure 3:
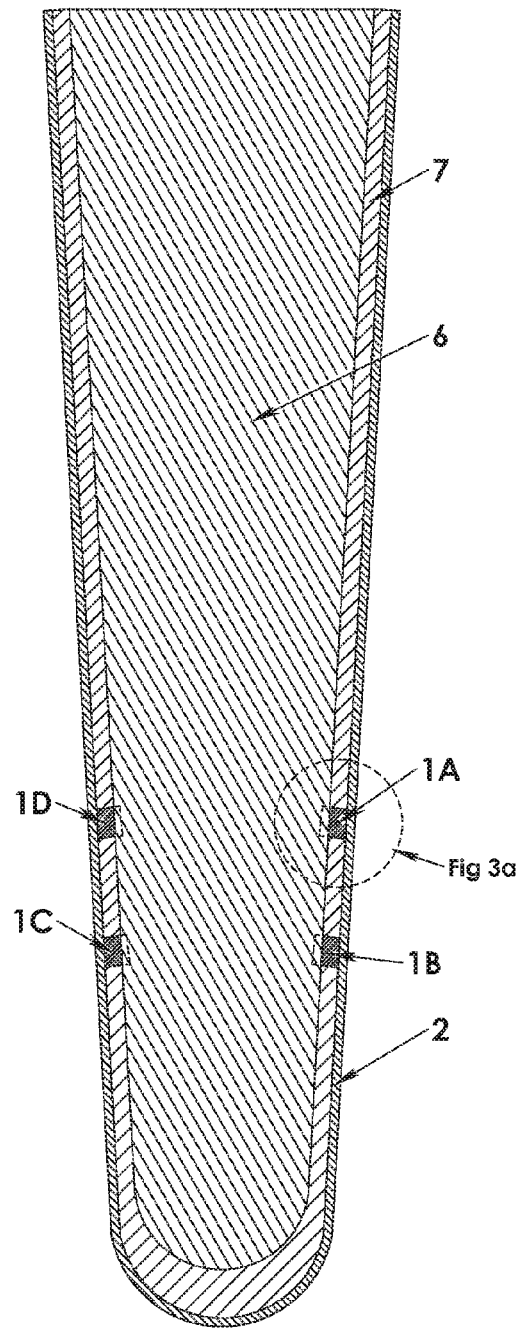

FIG. 3 is a sectional view of the liner interface of a preferred embodiment of the present invention once the tubular fabric layer has been placed inside the female portion of the molding machine and the male core portion of the molding machine has been inserted into the inside of the tubular fabric layer with the receptor patches axially deformed inside the mold as the core portion fills out the inside of the cavity.

Figure 3A:
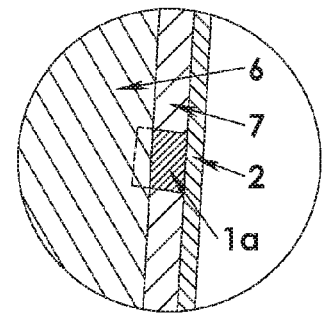

FIG. 3a is an enlarged sectional view of one of the receptors in FIG. 3 being compressed to some degree (shown in dashed lines) by the core prior to the molding process.

Figure 3B:
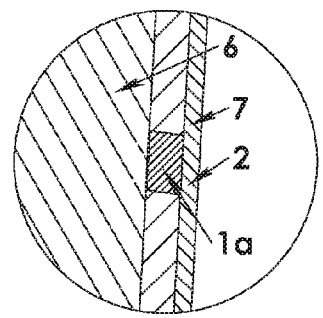

FIG. 3b is an enlarged view of another receptor in FIG. 3 that could alternatively be compressed very little or none at all to remain "flush" with the core during molding.

Figure 4:
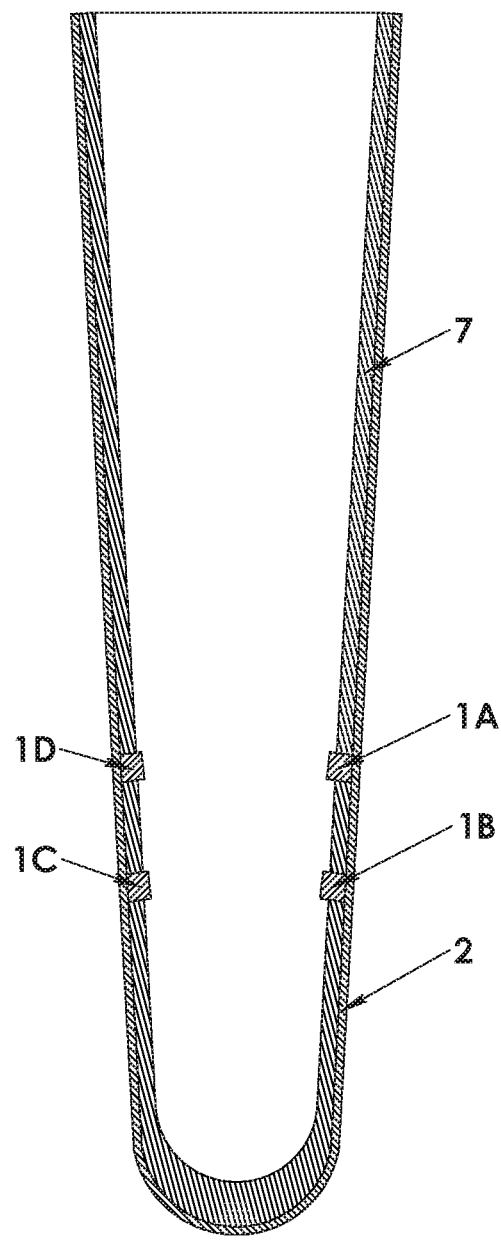

FIG. 4 is a sectional view of the liner interface of a preferred embodiment of the present invention that shows the once compressed patches returning to their full uncompressed shape after the injection molding process is completed.

DETAILED DESCRIPTION OF THE INVENTION

The present invention as illustrated in FIG. 2, includes a sewn fabric tubular layer (2) having longitudinal stretch characteristics of 5% to 180%, transverse stretch characteristics of 10% to 250%, and fabric thickness of 0.30 mm to 1.5 mm. As indicated by the dashed circle for illustrations shown in FIGS. 2a, 2b and 2c, a distal attachment in the region designated by numeral (3) may be attached to the distal end of the fabric tubular layer (2). As shown in FIG. 2a, a first embodiment of a distal attachment includes grommets (11) and an umbrella (12) assembly crimped to the closed end that is then encapsulated during the molding process. The umbrella assembly includes an outwardly extending threaded bore for receiving a threaded pin as part of a locking assembly. As shown in FIG. 2b, a second embodiment of a distal attachment is attached to the outer surface of the distal end of the fabric layer subsequent to the molding process and encapsulated thereto using a Liquid Silicone Rubber of approximately 60 durometer silicone to complete the distal attachment. While the liner illustrated includes the various distal attachments, exemplified in more detail in FIGS. 2a and 2b, it is important to note that the liner could alternatively be of the cushioned variety as in FIG. 2c, i.e., an interface without a distal attachment but reinforced with a distal cushioning element.

Referring to FIG. 2, the preferred receptor patches (1A-1D) are preferably made of non-compressible deformable Heat Resistant Silicone such as CLS 60-10 or any other low durometer silicone that is heat resistant and of a silicone that is either electrically conductive silicone, or non-electrically conductive silicone but individually wrapped with an electrically conductive medium (4A-4D) using any number of common adhesives such as traditional glue, bonding fabrics, fusible fabrics, or silicone based adhesives. Such electric conductive medium may preferably consist of Silver Fabric (or any other fabric or otherwise unobtrusive medium with low resistivity, including copper or carbon fabrics and/or light gauge wire), that covers each patch completely and includes strips (5A-5D) extending from each patch to encompass the length of the liner as a whole. The ends of these strips (5A-5D) can then be passed through the distal end of the liner to be connected to a CPU. Conversely, the conductive strips can also be fed out the proximal end of the liner, both the distal and proximal ends of the liner, or any other advantageous point throughout the liner to be affixed to a CPU for processing. The silicone patches and length of conductive strips are then strategically attached (glued, sewn, silicone based adhesive, etc.) to the inner surface of the fabric tubular layer prior to the placement of the fabric tubular layer into the female part of the molding machine. The silicone patches and strips are placed in specific pre-determined areas targeting specific nerve endings.

The preferred shape of the silicone patches is disc-shaped having an inward facing surface shaped as a dome with the periphery thereof tapered flush with the inner surface of the gel, whereby the dome extends slightly above the inner surface of the gel to improve contact on the nerve endings. However, other shapes can equally be employed, such as square-shaped, rectangle-shaped, diamond-shaped, oval-shaped or any other configuration necessary to accommodate the particular area to be sensed. Furthermore, the four patches illustrated in the figures is not intended to limit the number of patches that can be provided on any single liner which would depend of the type of prosthetic, orthotic or diagnostic equipment to be controlled. Also, the silicone discs are used for their properties highlighted above, but other heat resistant and deformable space fillers could potentially be wrapped in silver fabric (or substitute) and adhered to the fabric in a similar fashion such as heat resistant rubbers, etc.

As illustrated in FIG. 3, the male mold (6) is then lowered down into the center of the opened fabric tubular layer (2). The silicone discs (1A-1D) are now axially deformed a predetermined amount (preferably approximately 0.01"-0.25") by the male mold as denoted by the phantom lines in FIG. 3 and FIG. 3a. Alternatively, the discs (1A-1D) could be flush with the surface of the male mold (6) as demonstrated in FIG. 3b. Any combination of these options exist for any number of receptors. The amount of initial axial deformation (reduction in thickness) of the silicone discs would be predetermined by the amount of axial deformation (axial expansion) desired of the discs during the post molding process. It is noted that the molding procedure itself with the exception of the discs and strips is identical to the molding process of a traditional ALPS Locking Liner.

The Liner is then injection molded with the hot (300-400 degrees Fahrenheit) molten gel elastomer (7) exhibiting stretch characteristics of 600%-2,000% and a Modulus of 50-500 psi when cured. Such gel elastomers include silicone, thermoplastic elastomers [triblock], copolymer Styrenic gels, and polyurethane gels, etc. The preferred gel elastomer (7) is the ALPS elastomer but any of the above elastomers could be used in their molten stage to fill the annular space in the molding machine and completely engulf the silicone discs with the exception of the interface between the discs and male core part, and the strips thereby adhering to the inner surface of the tubular fabric layer, the discs and strips. Thus, the discs and the conductive strips are locked in place to ensure durability and an exact location.

As illustrated in FIG. 4, once the molding process is completed and the male portion of the mold is removed, the axially deformed silicone discs (1A-1D) will be free to axially expand. Due to the adhesion of the injected gel to the sides of the discs, the discs will not expand back to their initial thickness, but will expand back to an extent past the inner surface of the cured liner depending on the initial axial deformation of the discs during the molding process to thereby improve pressurized contact on the nerve endings while still being completely integrated into the inner liner material. The amount of axial expansion of the discs subsequent to the curing steps will depend on the amount of axial deformation exerted on the initial thickness of the discs during the molding process. The cured gel around the discs will thereby stabilize the receptor to the nerve ending when in use.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications and patent documents referenced herein are incorporated herein by reference in their entireties.

What is claimed is:

1. A liner interface with neural receptors comprising: a tubular fabric layer having an inner surface and an outer surface; at least one electrically conductive receptor comprising a non-compressible, deformable patch having an outer surface adapted to be attached to said fabric layer, an inner surface adapted to contact the skin of a user and side surfaces and a selective predetermined thickness between said inner and outer surfaces; said patch adapted to be electrically conductive; an electrically conductive element having a proximal end section extending from said at least one electrically conductive receptor for conducting electric signals therefrom caused by neural impulses from the nerve endings when said interface is in use and a distal end section; said outer surface of the structure of said at least one receptor and an outer surface of said proximal end section of said electrically conductive element themselves are attached only to said inner surface of said fabric layer at a selective location based on the area of the user to be sensed; said inner surface of said fabric and said side surfaces of said receptor and said electrically conductive element having a predetermined thickness of gel coated thereon; and wherein said predetermined thickness of said receptor is greater than or equal to said predetermined thickness of said gel material coating.

2. A liner interface with neural receptors as claimed in claim 1, wherein said at least one patch is made of non-compressible, deformable, heat-resistant, electrically conductive silicone material.

3. A liner interface with neural receptors as claimed in claim 2, wherein said electrically conductive element is embedded in said gel material coating and having one end extending into said electrically conductive receptor and an opposite end extending beyond said gel material coating.

4. A liner interface with neural receptors as claimed in claim 3, wherein said electrically conductive element comprises a material selected from the group consisting of carbon filament, copper filament, carbon fabric, copper fabric, silver thread, silver fabric or light gauge wire.

5. A liner interface with neural receptors as claimed in claim 1, wherein said at least one patch is made of non-compressible, deformable, heat-resistant, non-electrically conductive elastomeric material wrapped with an electrically conductive medium.

6. A liner interface with neural receptors as claimed in claim 5, wherein one or both of said electrically conductive medium and element comprise a material selected from the group consisting of carbon filament, copper filament, carbon fabric, copper fabric, silver thread, silver fabric or light gauge wire.

7. A liner interface with neural receptors as claimed in claim 6, wherein said electrically conductive element is formed as an extension of said electrically conductive medium.

8. A liner interface with neural receptors as claimed in claim 6, wherein said electrically conductive element is separate from but attached to said electrically conductive medium.

9. A liner interface with neural receptors as claimed in claim 7, wherein said electrically conductive element is embedded in said gel material coating and having one end being part of said wrapped electrically conductive medium and an opposite end extending beyond said gel material coating.

10. A liner interface with neural receptors as claimed in claim 8, wherein said electrically conductive element is embedded in said gel material coating and having one end being attached to said wrapped electrically conductive medium and an opposite end extending beyond said gel material coating.

11. A liner interface with neural receptors as claimed in claim 5, wherein said electrically conductive medium is adhered onto said electrically non-conductive material.

12. A liner interface with neural receptors as claimed in claim 1, wherein said patch is disc-shaped, square-shaped, rectangular-shaped, oval-shaped or diamond-shaped.

13. A liner interface with neural receptors as claimed in claim 1, wherein said gel material coating exhibits stretch characteristics of 600%-2000% and a Modulus of 50-500 psi when cured.

14. A liner interface with neural receptors as claimed in claim 1, wherein said gel material coating is comprised of a material selected from the group consisting of silicone, thermoplastic triblock elastomers, copolymer Styrenic gels and polyurethane gels.

15. A liner interface with neural receptors as claimed in claim 1, wherein said at least one receptor is axially deformable to approximately 0.25 inches beyond said predetermined thickness of said gel material coating.

16. A prosthetic liner with neural receptors comprising: a tubular fabric layer having an inner surface, an outer surface, a distal closed end and a proximal open end adapted to enclose a residual limb of an amputee; at least one electrically conductive receptor comprising a non-compressible deformable patch having an outer surface adapted to be attached to said fabric layer, an inner surface adapted to contact the skin of a user, and side surfaces and a selective predetermined thickness between said inner and outer surfaces; said patch adapted to be electrically conductive; an electrically conductive element having a proximal end section extending from said at least one electrically conductive receptor for conducting electric signals therefrom caused by neural impulses from nerve endings when said interface is in use and a distal end section; said outer surface of the structure of said at least one receptor and an outer surface of said proximal end section of said electrically conductive element themselves are attached only to said inner surface of said fabric layer at a selective location based on the area of the user to be sensed; said inner surface of said fabric and said side surfaces of said receptor and said electrically conductive element having a predetermined thickness of gel material coated thereon; and wherein said predetermined thickness of said receptor is greater than or equal to said predetermined thickness of said coating.

17. A prosthetic liner interface with neural receptors as claimed in claim 16, wherein said tubular fabric layer has longitudinal stretch characteristics of 5%-180%, transverse stretch characteristics of 10%-250%, and fabric thickness of 0.30 mm to 1.5 mm.

18. A prosthetic liner interface with neural receptors as claimed in claim 16, wherein a distal attachment is attached to an outer surface of said distal closed end of said tubular fabric layer and is encapsulated with liquid silicone rubber.

19. A prosthetic liner interface with neural receptors as claimed in claim 16, wherein a distal attachment is mounted through said distal closed end of said tubular fabric layer and extends partially within said distal closed end and partially beyond said distal closed end and is fastened thereto by grommets, wherein said portion of said distal attachment that is within said closed distal end of said tubular fabric is encapsulated with said gel material coating.

20. A prosthetic liner interface with neural receptors as claimed in claim 16, wherein said at least one patch is made of non-compressible, deformable, heat-resistant, electrically conductive silicone material.

21. A prosthetic liner interface with neural receptors as claimed in claim 20, wherein said electrically conductive element is embedded in said gel material coating and having one end extending into said electrically conductive receptor and an opposite end extending beyond said gel material coating.

22. A prosthetic liner interface with neural receptors as claimed in claim 21, wherein said electrically conductive element comprises a material selected from the group consisting of carbon filament, copper filament, carbon fabric, copper fabric, silver thread, silver fabric or light gauge wire.

23. A prosthetic liner interface with neural receptors as claimed in claim 16, wherein said at least one patch is made of non-compressible, deformable, heat-resistant, non-electrically conductive elastomeric material wrapped with electrically conductive medium.

24. A prosthetic liner interface with neural receptors as claimed in claim 23, wherein one or both of said electrically conductive medium and element comprise a material selected from the group consisting of carbon filament, copper filament, carbon fabric, copper fabric, silver thread, silver fabric or light gauge wire.

25. A prosthetic liner interface with neural receptors as claimed in claim 24, wherein said electrically conductive element is formed as an extension of said electrically conductive medium.

26. A prosthetic liner interface with neural receptors as claimed in claim 24, wherein said electrically conductive element is separate from but attached to said electrically conductive medium.

27. A prosthetic liner interface with neural receptors as claimed in claim 25, wherein said electrically conductive element is embedded in said gel material coating and having one end being part of said wrapped electrically conductive medium and an opposite end extending beyond said gel material coating.

28. A prosthetic liner interface with neural receptors as claimed in claim 26, wherein said electrically conductive element is embedded in said gel material coating and having one end being attached to said wrapped electrically conductive medium and an opposite end extending beyond said gel material coating.

29. A prosthetic liner interface with neural receptors as claimed in claim 23, wherein said electrically conductive medium is adhered onto said electrically non-conductive material.

30. A prosthetic liner interface with neural receptors as claimed in claim 16, wherein said patch is disc-shaped, square-shaped, rectangular-shaped, oval-shaped or diamond-shaped.

31. A prosthetic liner interface with neural receptors as claimed in claim 16, wherein said gel material coating exhibits stretch characteristics of 600%-2000% and a Modulus of 50-500 psi when cured.

32. A prosthetic liner interface with neural receptors as claimed in claim 16, wherein said gel material coating is comprised of a material selected from the group consisting of silicone, thermoplastic triblock elastomers, copolymer Styrenic gels and polyurethane gels.

33. A prosthetic liner interface with neural receptors as claimed in claim 16, wherein said at least one receptor is axially deformable to approximately 0.25 inches beyond said predetermined thickness of said gel material coating.

34. A method of making a liner interface with neural receptors as defined in claim 1, comprising: providing said tubular fabric layer having an inner surface and an outer surface; providing said at least one electrically conductive receptor comprising a non-compressible, deformable patch having an outer surface adapted to be attached to said fabric layer, an inner surface adapted to contact the skin of a user and a selective predetermined thickness between said inner and outer surfaces; said patch adapted to be electrically conductive; providing said electrically conductive element having a proximal end section extending from said at least one electrically conductive receptor for conducting electric signals caused by neural impulses from nerve endings when said interface is in use and a distal end section;

attaching the outer surface of the structure of said at least one receptor and an outer surface of said proximal end section of said electrically conductive element themselves only to said inner surface of said fabric layer at a selective location based on the area of the user to be sensed;

securing said outer surface of said fabric layer onto a first part of a molding machine having a predetermined shape;

applying a second part of said molding machine complementally configured to the predetermined shape of the first part toward said inner surface of said fabric layer to an extent to abut said at least one receptor or where the at least one receptor is axially deformed to a predetermined degree and a space exists between the inner surface of the fabric layer and the second part;

injecting a molten gel into said space to fill said space, adhere to said inner surface of said fabric layer, and engulf the portions of said at least one receptor and said electrically conductive element that are exposed to said molten gel such that said at least one receptor is free of said molten gel along the interface between said receptor and said second part;

allowing said gel to cure to form a gel material coating with a gel material coating inner surface;

removing said second part from said first part; and permitting said at least one receptor to remain flush with or to expand beyond the inner surface of said gel material coating to thereby provide an improved pressurized contact on a selective nerve ending when said liner interface is applied against a body part of a user.

35. A method of making a liner interface with neural receptors as claimed in claim 34, wherein said at least one patch is made of non-compressible, deformable, heat-resistant, electrically conductive silicone material.

36. A method of making a liner interface with neural receptors as claimed in claim 34, wherein said electrically conductive element is embedded in said gel material coating and having one end extending into said electrically conductive material and an opposite end extending beyond said cured gel material coating.

37. A method of making a liner interface with neural receptors as claimed in claim 36, wherein said electrically conductive element comprises a material selected from the group consisting of carbon filament, copper filament, carbon fabric, copper fabric, silver thread, silver fabric or light gauge wire.

38. A method of making a liner interface with neural receptors as claimed in claim 34, wherein said at least one patch is made of non-compressible, deformable, heat-resistant, non-electrically conductive elastomeric material wrapped with electrically conductive medium.

39. A method of making a liner interface with neural receptors as claimed in claim 38, wherein one or both of said electrically conductive medium and element comprises a material selected from the group consisting of carbon filament, copper filament, carbon fabric, copper fabric, silver thread, silver fabric or light gauge wire.

40. A method of making a liner interface with neural receptors as claimed in claim 39, wherein said electrically conductive element is formed as an extension of said electrically conductive medium.

41. A method of making a liner interface with neural receptors as claimed in claim 39, wherein said electrically conductive element is separate from but attached to said electrically conductive medium.

42. A method of making a liner interface with neural receptors as claimed in claim 40, wherein said electrically conductive element is embedded in said cured gel and having one end being part of said wrapped electrically conductive medium and an opposite end extending beyond said gel material coating.

43. A method of making a liner interface with neural receptors as claimed in claim 41, wherein said electrically conductive element is embedded in said cured gel and having one end being attached to said wrapped electrically conductive medium and an opposite end extending beyond said gel material coating.

44. A method of making a liner interface with neural receptors as claimed in claim 38, wherein said electrically conductive medium is adhered onto said electrically non-conductive material.

45. A method of making a liner interface with neural receptors as claimed in claim 34, wherein said patch is disc-shaped, square-shaped, rectangular-shaped, oval-shaped or diamond-shaped.

46. A method of making a liner interface with neural receptors as claimed in claim 34, wherein said molten gel is injected into said space at 300-400 degrees Fahrenheit.

47. A method of making a liner interface with neural receptors as claimed in claim 34, wherein said gel material coating exhibits stretch characteristics of 600%-2000% and a Modulus of 50-500 psi when cured.

48. A method of making a liner interface with neural receptors as claimed in claim 34, wherein said gel material coating is comprised of a material selected from the group consisting of silicone, thermoplastic triblock elastomers, copolymer Styrenic gels and polyurethane gels.

49. A method of making a liner interface with neural receptors as claimed in claim 34, wherein said at least one receptor is axially deformed to said predetermined degree such that said at least one patch axially expands approximately 0.0 inches to 0.25 inches during said permitting step.

50. A method of making a prosthetic liner interface with neural receptors as defined in claim 16, comprising: providing said tubular fabric layer having an inner surface, an outer surface, a distal closed end and a proximal open end adapted to enclose a residual limb of an amputee; providing said at least one electrically conductive receptor comprising a non-compressible deformable patch having an outer surface adapted to be attached to said fabric layer, an inner surface adapted to contact the skin of a user, and a selective predetermined thickness between said inner and outer surfaces; said patch adapted to be electrically conductive; providing said electrically conductive element having a proximal end section extending from said at least one electrically conductive receptor for conducting electric signals caused by neural impulses from nerve endings when said interface is in use and a distal end section; attaching said outer surface of the structure of said at least one receptor and an outer surface of said proximal end section of said electrically conductive element themselves only to said inner surface of said fabric layer at a selective location based on the area of the user to be sensed; securing said outer surface of said tubular fabric onto a female part of a molding machine designed to be complementally shaped to the desired shape of the prosthetic liner interface; inserting a male core part of said molding machine complementally configured to the shape of the female part into said tubular fabric layer to an extent to abut said at least one receptor or where the at least one receptor is axially deformed to a predetermined degree and an annular space exists between the inner surface of the tubular fabric layer and the male part; injecting a molten gel into said annular space to completely fill said annular space, adhere to said inner surface of said fabric layer, and engulf the portions of said at least one receptor and said electrically conductive element that are exposed to said molten gel such that said at least one receptor is free of said molten gel along the interface between said receptor and said male core part; allowing said gel to cure to form a gel material coating with a gel material coating inner surface; removing said male core part from said female part; and permitting said at least one receptor to remain flush with or to expand beyond the inner surface of said gel material coating to thereby provide an improved pressurized contact on a selective nerve ending when said liner interface is donned on a user.

51. A method of making a prosthetic liner interface with neural receptors as claimed in claim 50, wherein said tubular fabric layer has longitudinal stretch characteristics of 5%-180%, transverse stretch characteristics of 10%-250%, and fabric thickness of 0.30 mm to 1.5 mm.

52. A method of making a prosthetic liner interface with neural receptors as claimed in claim 50, wherein a distal attachment is attached to an outer surface of said distal closed end of said tubular fabric layer subsequent to said removing step and is encapsulated with liquid silicone rubber.

53. A method of making a prosthetic liner interface with neural receptors as claimed in claim 50, wherein a distal attachment is mounted through said distal closed end of said tubular fabric layer prior to said securing step and extends partially within said distal closed end and partially beyond said distal closed end and is fastened thereto by grommets, wherein said portion of said distal attachment that is within said closed distal end of said tubular fabric is encapsulated with said injected molten gel.

54. A method of making a prosthetic liner interface with neural receptors as claimed in claim 50, wherein said at least one electrically conductive patch is made of non-compressible, deformable, heat-resistant, electrically conductive silicone material.

55. A method of making a prosthetic liner interface with neural receptors as claimed in claim 54, wherein said electrically conductive element is embedded in said gel material coating and having one end extending into said electrically conductive material and an opposite end extending beyond said gel material coating.

56. A method of making a prosthetic liner interface with neural receptors as claimed in claim 55, wherein said electrically conductive element comprises a material selected from the group consisting of carbon filament, copper filament, carbon fabric, copper fabric, silver thread, silver fabric or light gauge wire.

57. A method of making a prosthetic liner interface with neural receptors as claimed in claim 50, wherein said at least one patch is made of non-compressible, deformable, heat-resistant, non-electrically conductive elastomeric material wrapped with electrically conductive medium.

58. A method of making a prosthetic liner interface with neural receptors as claimed in claim 57, wherein one or both of said electrically conductive medium and element comprises a material selected from the group consisting of carbon filament, copper filament, carbon fabric, copper fabric, silver thread, silver fabric or light gauge wire.

59. A method of making a prosthetic liner interface with neural receptors as claimed in claim 58, wherein said electrically conductive element is formed as an extension of said electrically conductive medium.

60. A method of making a prosthetic liner interface with neural receptors as claimed in claim 58, wherein said electrically conductive element is separate from but attached to said electrically conductive medium.

61. A method of making a prosthetic liner interface with neural receptors as claimed in claim 59, wherein said electrically conductive element is embedded in said cured gel and having one end being part of said wrapped electrically conductive medium and an opposite end extending beyond said cured gel.

62. A method of making a prosthetic liner interface with neural receptors as claimed in claim 60, wherein said electrically conductive element is embedded in said cured gel and having one end being attached to said wrapped electrically conductive medium and an opposite end extending beyond said cured gel.

63. A method of making a prosthetic liner interface with neural receptors as claimed in claim 57, wherein said electrically conductive medium is adhered onto said electrically non-conductive material.

64. A method of making a prosthetic liner interface with neural receptors as claimed in claim 50, wherein said patch is disc-shaped, square-shaped, rectangular-shaped, oval-shaped or diamond-shaped.

65. A method of making a prosthetic liner interface with neural receptors as claimed in claim 50, wherein said molten gel is injected into said space at 300-400 degrees Fahrenheit.

66. A method of making a prosthetic liner interface with neural receptors as claimed in claim 50, wherein said gel material coating exhibits stretch characteristics of 600%-2000% and a Modulus of 50-500 psi when cured.

67. A method of making a prosthetic liner interface with neural receptors as claimed in claim 50, wherein said gel material coating is comprised of a material selected from the group consisting of silicone, thermoplastic triblock elastomers, copolymer Styrenic gels and polyurethane gels.

68. A method of making a prosthetic liner interface with neural receptors as claimed in claim 50, wherein said at least one receptor is axially deformed to said predetermined degree such said at least one patch axially expands approximately 0.0 inches to 0.25 inches during said permitting step.

* * * * *